United States Patent [19]

Obikawa et al.

[11] Patent Number: 5,354,502
[45] Date of Patent: Oct. 11, 1994

[54] 1,3-DIOXANE DERIVATIVE AND LIQUID CRYSTAL COMPOSITIONS CONTAINING IT

[75] Inventors: Tsuyoshi Obikawa; Shuji Ikukawa; Jitsuko Nakayama, all of Suwa, Japan

[73] Assignee: Seiko Epson Corporation, Tokyo, Japan

[21] Appl. No.: 986,653

[22] Filed: Dec. 8, 1992

Related U.S. Application Data

[62] Division of Ser. No. 651,269, filed as PCT/JP90/01318, Oct. 12, 1989, abandoned.

[30] Foreign Application Priority Data

| Oct. 12, 1989 | [JP] | Japan | 1-265664 |
| Oct. 20, 1989 | [JP] | Japan | 1-273078 |
| Dec. 19, 1989 | [JP] | Japan | 1-329056 |

[51] Int. Cl.$^5$ ............ C09K 19/34; C07D 319/06; C07D 407/00
[52] U.S. Cl. ............ 252/299.61; 549/369; 549/370
[58] Field of Search ............ 549/369, 370; 252/299.61

[56] References Cited

U.S. PATENT DOCUMENTS

| 4,348,324 | 9/1982 | Demus et al. | 549/369 |
| 4,486,332 | 12/1984 | Demus et al. | 252/299.61 |
| 4,551,264 | 11/1985 | Eidenschink et al. | 252/299.62 |
| 4,659,502 | 4/1987 | Fearon et al. | 252/299.61 |
| 4,704,227 | 11/1987 | Krause et al. | 252/299.61 |
| 4,726,911 | 2/1988 | Krause et al. | 252/299.61 |
| 4,755,323 | 7/1988 | Eidenschink et al. | 252/299.61 |
| 4,853,152 | 8/1989 | Goto | 252/299.63 |
| 5,026,879 | 6/1991 | Obikawa | 549/369 |

FOREIGN PATENT DOCUMENTS

| 0205503 | 3/1989 | European Pat. Off. |
| 0400861 | 12/1990 | European Pat. Off. |
| 56-100886 | 8/1981 | Japan |
| 62-501216 | 5/1987 | Japan |
| 2105717 | 3/1983 | United Kingdom |

OTHER PUBLICATIONS

E. Kleinpeter, et al., Liquid-Crystalline Behaviour of 2,5-Disubstituted 1,3-Dioxanes Subject to the Flexibility of Terminal Chain, 4 Nov. 1987.

H.-M. Vorbrodt, et al., New Liquid Crystalline 2,5-Disubstituted 1,3-Dithians and 1,3-Dioxanes, Jul. 19, 1984.

*Primary Examiner*—Robert L. Stoll
*Assistant Examiner*—C. Harris
*Attorney, Agent, or Firm*—Stroock & Stroock & Lavan

[57] ABSTRACT

A 1,3-dioxane derivative and a liquid crystal composition containing it as expressed by the general formula $$R-\langle H \rangle-(A)_n-\langle\text{dioxane}\rangle-\langle\text{Ar}(F)(F)\rangle-CN \quad (I)$$

(where R is a straight chain alkyl group of carbon number 1 to 10, A is a single bond or —$CH_2CH_2$— group, n is 0 or 1, and the cyclohexane ring and 1,3-dioxane ring are respectively in trans form is disclosed.) The 1,3-dioxane derivative represented by general formula (I) has a very large dielectric anisotropy and a small birefringence. Liquid crystal compositions containing (I) can be driven at low voltage and will provide a liquid crystal display apparatus with a wide visual angle.

3 Claims, No Drawings

1,3-DIOXANE DERIVATIVE AND LIQUID CRYSTAL COMPOSITIONS CONTAINING IT

This application is a division of application Ser. No. 07/651,269, filed as PCT/JP90/01318, Oct. 12, 1989, now abandoned.

FIELD OF TECHNOLOGY

The present invention relates to a 1,3-dioxane derivative and liquid crystal compositions containing it used as Np type constituents of large dielectric constant anisotropy ($\Delta\epsilon$), among the constituents that construct nematic liquid crystal compositions used in liquid crystal display apparatus.

BACKGROUND OF THE TECHNOLOGY

Liquid crystal apparatuses that utilize the electro-optical effect of nematic liquid crystals are being applied in a wider range than priorly. Their display systems include such as dynamic scattering types, quest-host types, twisted nematic types (TN types) and supertwisted nematic types (STN types), and the methods used to drive these display apparatuses include such as static drive systems, time sharing drive systems (dynamic drive systems), active matrix drive systems and 2-frequency drive systems.

The main characterizing features of TN types and STN types that make them superior to emission types of display apparatus such as LED, EL and CRT are such as the following.

(1) Miniaturization and thinning are possible.
(2) Drive voltage is low, and power consumption is very little.
(3) Phasing with LSI is good, and the drive circuit can be simplified.
(4) Because they are light receivers, they are easily seen in direct daylight, and do not cause eyestrain even under long periods of use.

Making the best use of these characterizing features, TN type display apparatuses are being widely applied in displays for such as watches, desk calculators, audio instruments, games, automobile dashboards, cameras, telephone instruments and various types of measuring instruments, and it is estimated that these fields of application will continue to broaden in the future.

Liquid display apparatuses have had their display capacities (number of scanning lines) expanded compared to prior art, together with the expansion in their fields of application. With TN type display apparatuses having time sharing drive systems, the number of scanning lines has a limit on the order of 200, and STN types and TN types with active matrix drive systems are being developed as display systems to replace them. At the present time STN systems are being applied to word processor and personal computer displays and TN types with active matrix drive systems are being applied to liquid crystal color televisions, with the prior main focus being as display apparatuses replacing CRT's.

The various properties indicated below are what are considered to be the indispensable requirements in TN type or STN type liquid crystal display apparatus for such applications, with the understanding that the properties of the liquid crystal materials used in these liquid crystal display apparatuses have various differences in such as their fields of application, display systems and drive methods.

(1) They must have thermal, optical, electrical and chemical stability, without coloration.

(2) They must have a practical temperature range as wide as possible in the vicinity of room temperature.

(3) The threshold value ($V_{th}$) of the voltage-light transmission properties (V-$I_o$ properties) must be low, and the temperature dependence ($\Delta T$) must be little.

(4) The steepness ($\beta$) of V-$I_o$ should be as sharp as possible.

(5) The visual angle dependence ($\alpha$) of V-$I_o$ should be as small as possible.

(6) The electro-optical response speed should be fast.

Many liquid crystal compounds and liquid crystal analog compounds are known that satisfy (1) among these various properties, but at present none are known that satisfy the properties from (2) down with a single constituent liquid crystal compound. The actual situation is that liquid crystal compositions containing mixtures of plural nematic liquid crystal mixtures or their analogs are used to satisfy these properties.

After comparing the relation between the properties listed above against the display capacities (number of scanning lines) of the TN type liquid crystal display apparatuses with time sharing drives that are now most widely used, the indispensable requirements for high time sharing drives are these three.

(1) Steepness must be sharp.
(2) $V_{th}$ temperature dependence must be small.
(3) Visual angle dependence must be little. Considering LSI voltage capacity and power source voltage, there is also this important condition.
(4) The $V_{th}$ must be low.

These various conditions will be explained next. First, steepness ($\beta$) will be represented as $V_{th}$ and $V_{sat}$ $$\beta = \frac{V_{sat}}{V_{th}}$$

Here $V_{th}$ and $V_{sat}$ are the voltages when the light transmissivity is respectively 10% and 90%.

Ideally $\beta=1$, but it is actually on the order of $\beta=1.3$ to 1.5, and it is difficult to develop liquid crystal compounds having a $\beta$ smaller than this value. In the case of the TN type, it is known that $\beta$ decreases as the value of $K_{33}/K_{11}$ decreases, and it is reported that $K_{33}/K_{11}$ is small in liquid crystal compounds having pyrimidine structures. Here, $K_{11}$ and $K_{33}$ are respectively the splay and bend elastic constants.

$V_{th}$ is expressed ideally for the TN type as follows.

$$V_{th} = \frac{\pi}{d} \sqrt{\frac{K_{11} + (K_{33} - K_{22})/4}{\epsilon_o \Delta\epsilon}}$$

Here d is the thickness of the liquid crystal layer, $K_{11}$, $K_{22}$ and $K_{33}$ are respectively the splay, twist and bend constants of elasticity, and $\epsilon_o$ represents the permitivity of vacuum.

Consequently, to lower $V_{th}$, the constant of elasticity should be small and a liquid crystal compound having a large $\Delta\epsilon$ should be added. Also, the temperature dependence ($\Delta T$) of $V_{th}$ generally shows a tendency for the $V_{th}$ to lower along with rises in temperature, and has the particular characteristic of dropping sharply in the vicinity of the N-I point. This is because of the temperature dependence of the constant of elasticity.

Visual angle dependence ($\alpha$) is a particular property of the TN type or the STN type, and its cause is said to lie in the pretilt arising between the liquid crystal and the surface given orientation treatment.

α can be improved by making the thickness of the liquid crystal layer thinner and making the Δn of the liquid crystal composition smaller.

In this regard, known liquid crystal compounds having a large Δε and a small Δn that were used for these purposes priorly are shown next.

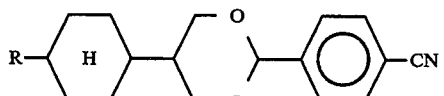
(A)

H-M. Vorbrodt, et al., Mol. Cryst. Lig. Cryst., 123, 137 (1985)

and

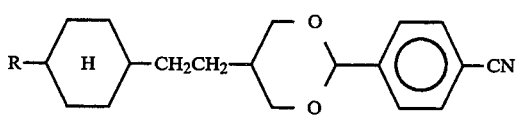
(B)

E. Kleinpeter, et al., Tetrahedron, 44, 1609 (1988)

These liquid crystal compounds have high N-I points and small Δn, but they have the defects of a small Δε and poor compatibility with other liquid crystal compounds.

DISCLOSURE OF THE INVENTION

The object of the present invention lies in offering a compound having a large Δε, a small Δn, and good compatibility with other liquid crystal compounds.

Another object of the present invention lies in offering a liquid crystal composition capable of high time sharing drive under low voltage, by mixing the said compound with another liquid crystal composition.

The present invention is a 1,3-dioxane derivative represented by the following general formula

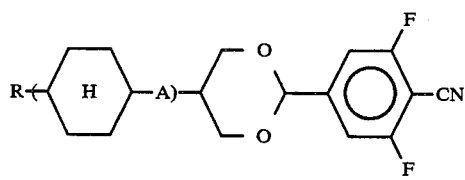
(1)

(where R is a straight chain alkyl group with 1 to 10 carbon atoms, A represents a single bond or a —CH$_2$CH$_2$— group, and the cyclohexane ring and 1,3-dioxane ring are respectively trans configurations and n is 0 or 1). It includes the following three types of compounds.

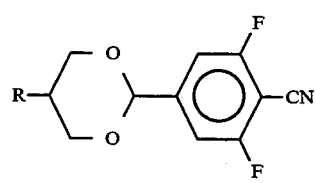
(1-a)

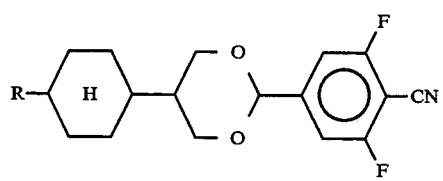
(1-b)

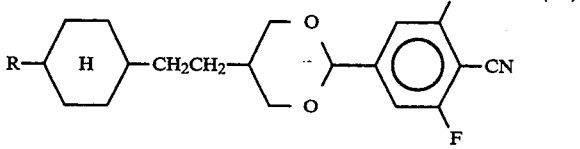
(1-c)

(where R represents a straight chain alkyl group with 1 to 10 carbon atoms, and the cyclohexane ring and 1,3-dioxane ring are trans configurations.)

Also, the 1,3-dioxane derivative of the present invention is contained as at least one of the ingredients in the liquid crystal composition of the present invention.

Although compound (1-a) of the present invention has no liquid crystal phase, its Δε is very large and its Δn is small, so that it is very effective in lowering the V$_{th}$ of the liquid crystal composition. Compounds (1-b) and (1-c) have nematic phases, and since their Δε are considerably large and their Δn are small, they can be used as the main ingredients of liquid crystal compositions, making it possible to obtain liquid crystal compositions having low V$_{th}$ and small Δn and that are capable of high time sharing drive.

Also, the compound of the present invention has good compatibility with other liquid crystal compounds, and when done suitably it can be mixed with other liquid crystal compounds in proportions of 1 to 60wt %, although it is preferred to have a range of 1 to 30 wt % when the object is to mix it with all of the prior liquid crystal compounds.

Further, when mixing the compound of the present invention with other liquid crystal compounds, while the objects will be achieved by using the compound of the present invention as a single ingredient, but it will be more effective to use it mixed as plural ingredients for lowering the melting point in eutectic compositions.

There are no restrictions as to the prior liquid crystal compounds that are capable of being mixed with the compound of the present invention, and liquid crystal compounds of the following systems may be considered for such mixture.

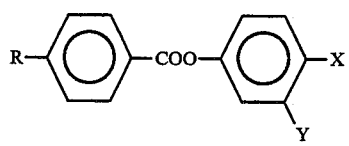

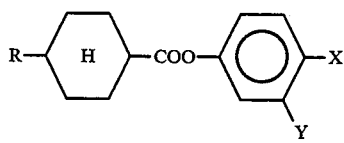

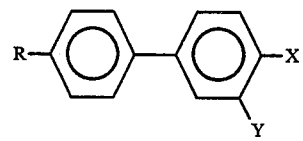

-continued

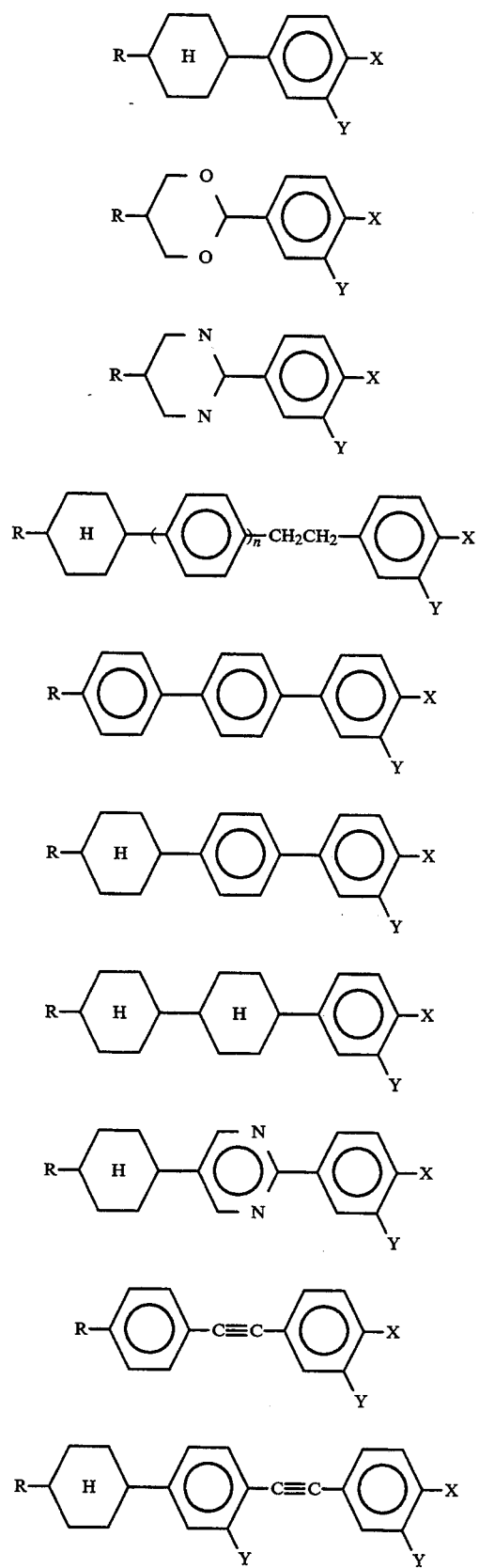

(where, R is a straight chain alkyl group or alkoxy group, X is a straight chain alkyl group, alkoxy group, CN or F, Y is H, F or Cl and n is 0 or 1).

The method of manufacturing the 1,3-dioxane derivative of the present invention will be discussed next.

With the present invention, the compound shown by the general formula

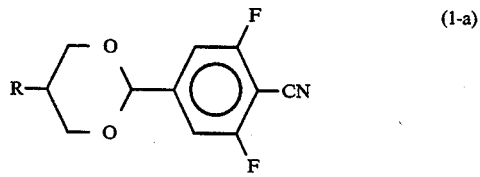

(1-a)

(where R is a straight chain alkyl group of 1 to 10 carbon atoms, and the 1,3-dioxane ring has a trans configuration) can be manufactured by Schemes 1, 2 and 3 below.

Scheme 1

(2)

Step 1-1 | $CH_2(COOC_2H_5)_2$, $NaOC_2H_5/C_2H_5OH$

R—CH(COOC$_2$H$_5$)$_2$ (3)

Step 1-2 | LiAlH$_4$/THF

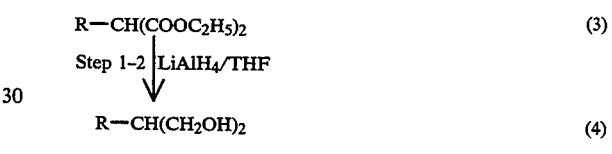

R—CH(CH$_2$OH)$_2$ (4)

In Scheme 1, the starting material is bromoalkane, and 2-alkylpropane-1,3-diol is obtained by a two stage reaction. In Scheme 2, the starting material is 6-dibromoaniline and 4-bromo-3,5-difluorobenzaldehyde is obtained by a four stage reaction. In Scheme 3, trans-2-(4'-cyano-3',5'-difluorophenyl)-5-alkyl-1,3-dioxane (1-a) of the present invention is obtained by a two stage reaction from 2-alkylpropane-1,3-diol and 4-bromo-3,5-difluorobenzaldehyde.

The method of manufacturing the compound (1-a) will next be explained overall in the order of the steps.

Step 1-1. Diethyl alkylmalonate (3) is obtained by an alkylation reaction of bromoalkane (2) and diethyl malonate in anhydrous ethanol under presence of sodium ethoxide (NaOC$_2$H$_5$).

Step 1-2. 2-alkylpropane-1,3-diol (4) is obtained by reducing compound (3) using lithium aluminum hydride (LiAlH$_4$) in anhydrous tetrahydrofuran (THF).

SCHEME 2

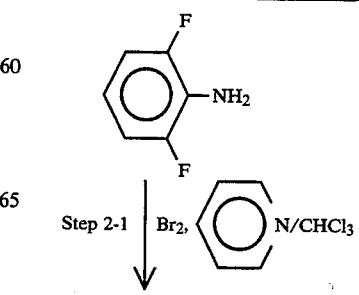

(5)

Step 2-1 | Br$_2$, N/CHCl$_3$

SCHEME 2 -continued

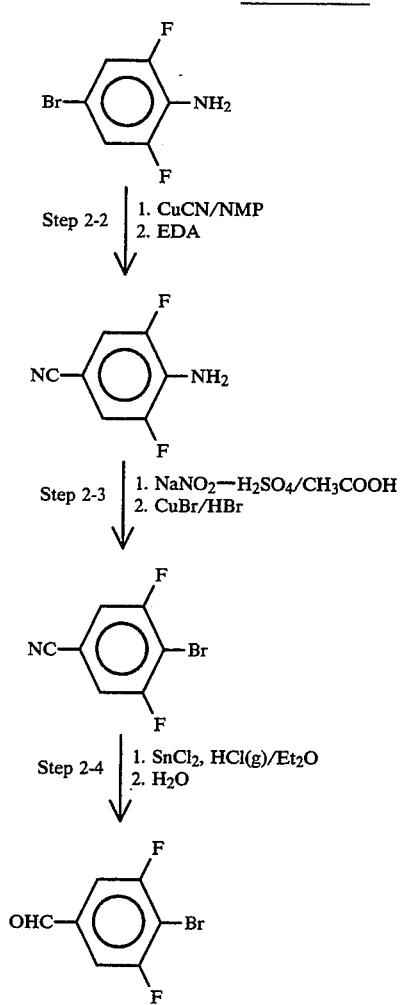

Step 2-1. 4-bromo-2,6-difluoroaniline (6) is obtained by bromination of 2,6-difluoroaniline (5) using bromine in chloroform under presence of anhydrous pyridine.

Step 2-2. 4-amino-3,5-difluorobenzonitrile (7) is obtained by cyanating compound (6) using copper cyanide (I) (CuCN) in N-methyl-2-pyrolidinone (NMP), and decomposing the nitrile copper complex of nitrile obtained using ethylene diamine (EDA).

Step 2-3. 4-bromo-3,5-difluorobenzonitrile (8) is obtained by diazotization of compound (7) using nitrocyl hydrogen sulfate ($HCO_4$—$ONO_2$) prepared from sodium nitrite ($NaNO_2$) and concentrated sulfuric acid in glacial acetic acid, and by bromination of this diazonium salt using copper bromide (I) in hydrobromic acid.

Step 2-4. 4-bromo-3,5-difluorobenzaldehyde (9) is obtained by reducing compound (8) by using tin chloride (II) in diethyl ether saturated with hydrogen chloride gas, and decomposing the tin complex of the imine thus formed with water.

SCHEME 3

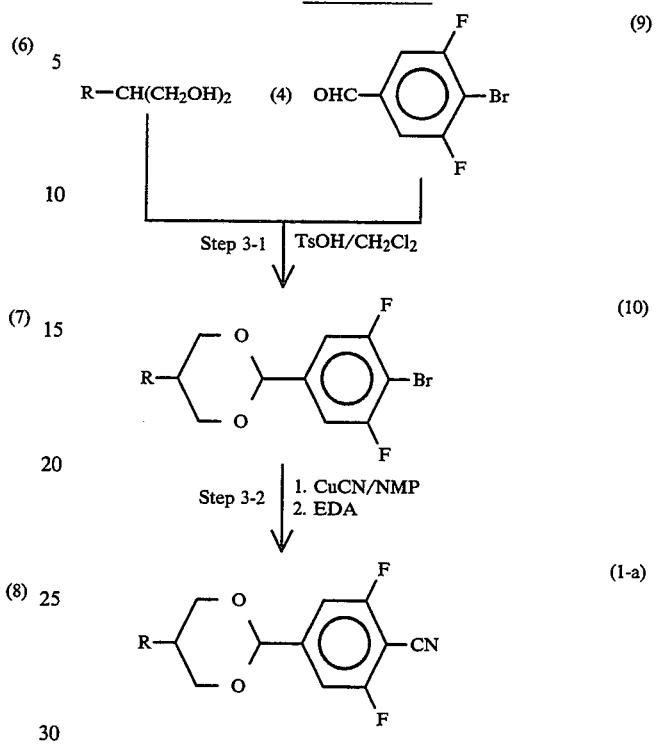

(where R is a straight chain alkyl group of 1 to 10 carbon atoms, and the 1,3-dioxane ring is a trans configuration.)

Step 3-1. 2-(4'-bromo-3',5'-difluorophenyl)-2-alkyl-1,3-dioxane (10) is obtained by a dehydration reaction of compound (4) and compound (9) with p-toluene sulfonic acid as a catalyst in dichloromethane.

Step 3-2. The compound of the present invention trans-2-(4'-cyano-3',5'-difluorophenyl)-2-alkyl-1,3-dioxane is obtained by cyanotizing compound (10) using CuCN in NMP and decomposing the copper complex of nitrile thus produced using EDA.

With the present invention the compound shown by the general formula

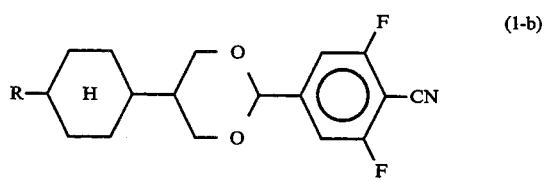

(where, R shows a straight chain alkyl group with a carbon number from 1 to 10, and the cyclohexane ring and the 1,3-dioxane ring has a trans configuration) can be made for example by the process shown in Schemes 2 and 4.

In Scheme 4, 2-(trans-4'-alkylcyclohexyl)propane-1,3-diol is obtained by a 3-stage reaction with 4-alkylcyclohexanol as the starting material. In Scheme 2, 4-bromo-3,5-difluorobenzaldehyde is obtained by a 4-stage reaction with 2,6-difluoroaniline as the starting material. In Scheme 5, the liquid crystal compound trans-2-(4'-cyano-3',5'-difluorophenyl)-5-(trans-4'-alkylcyclohexyl)-1,3-dioxane (1-b) of the present invention is obtained by a 2-stage reaction from 2-(trans-4'-alkylcyclohexyl)propane-1,3-diol and 4-bromo-3,5-difluorobenzaldehyde.

A summary of the method of making compound (1-b) following the step sequence will be explained next. Steps 2-1 through 2-4 were already explained in the method of making compound (1-a) and so will be abbreviated here.

SCHEME 4

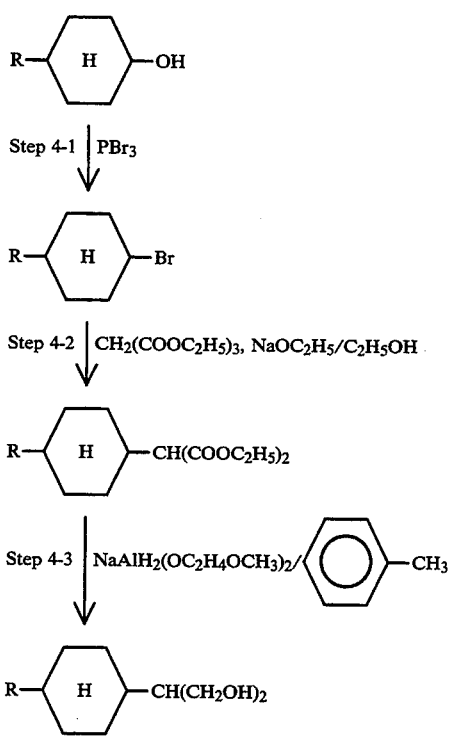

(where, R shows a straight chain alkyl group of carbon number 1 to 10, and the cyclohexane ring is a mixture of cis and trans compound.)

Step 4-1. 4-alkylcyclohexanol (11) is brominated using phosphorus tribromide to obtain 4-alkylbromocyclohexane (12).

Step 4-2. Compound (12) and diethyl malonate are given an alkylation reaction using NaOC$_2$H$_5$ in ethanol anhydride to obtain diethyl 4-alkylcyclohexylmalonate (13).

Step 4-3. Compound (13) is reduced using hydrogenated bis(methoxyethoxy) aluminum sodium hydride in toluene to obtain 2-(4'-alkylcyclohexyl)propane-1,3-diol (14).

SCHEME 5

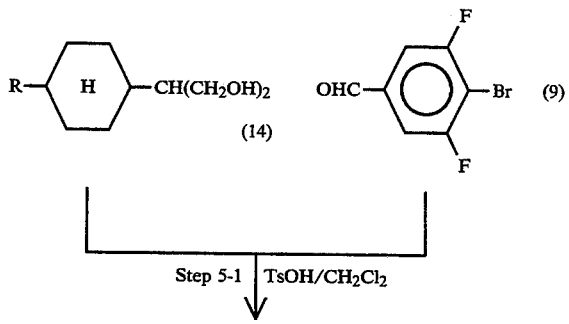

-continued
SCHEME 5

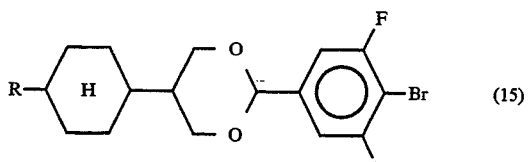

(where, R shows a straight chain alkyl group of carbon number 1 to 10, and the cyclohexane ring and 1,3-dioxane ring have trans configuration.)

Step 5-1. Compound (14) and compound (9) are given a dehydration reaction with TsOH as a catalyst in dichloromethane in the same manner as in Step 3 to obtain 2-(4'-bromo-3',5'-difluorophenyl)-5-(4'-alkylcyclohexyl)-1,3-dioxane (15).

Step 5-2. Compound (15) is cyanated using CuCN in NMP in the same manner as in Step 3-2, and the nitrile copper complex of nitrile formed is decomposed with EDA to obtain trans-2-(4'-cyano-3',5'-difluorophenyl)-5-(trans-4'-alkylcyclohexyl)-1,3-dioxane (1-b) of the present invention.

Again, with the present invention, the compound shown by the general formula

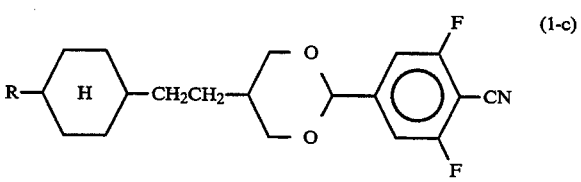

(where, R shows a straight chain alkyl group of carbon number 1 to 10, and the cyclohexane ring and 1,3-dioxane ring has a trans configuration) can be made for example by the next process as shown in Schemes 2, 6 and 7.

Scheme 2 was explained with compound (1-a) and so may be abbreviated. In Scheme 6, 2-[2'-(trans-4''-alkylcyclohexyl)ethyl]propane-1,3-diol is obtained by an 8-stage reaction with trans-4-alkylcyclohexanecarboxylic acid as the starting material. In Scheme 7, the trans-2-(4'-cyano-3',5'-difluorophenyl)-5-[2'-(trans-4''-alkylcyclohexyl)ethyl]-1,3-dioxane (1-c) of the present invention is obtained by a 2-stage reaction from 2-[2'-(trans-4''-alkylcyclohexyl)ethyl]propane-1,3-diol and 4-bromo-3,5-difluorobenzaldehyde.

A summary of the method of making compound (1-c) following the order of steps will be explained below. Steps 2-1 to 2-4 were already explained in the method of making compound (1-a) and so will be abbreviated.

SCHEME 6

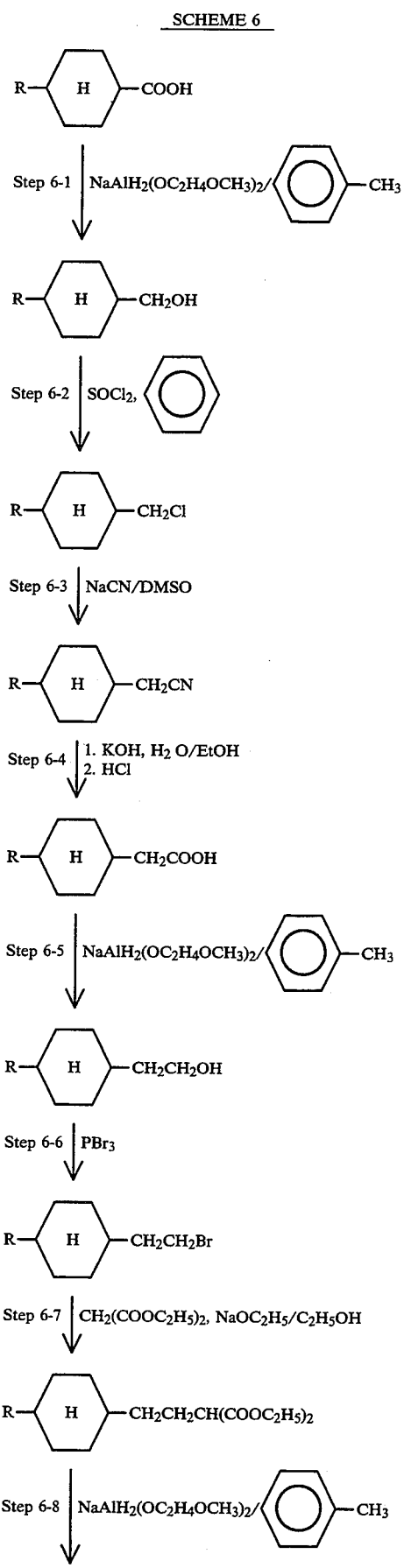

-continued
SCHEME 6

(24) R—[H]—CH₂CH₂CH(CH₂OH)₂

(where, R shows a straight chain alkyl group of carbon number 1 to 10, and the cyclohexane ring has a trans configuration.)

SCHEME 7

(17) R—[H]—CH₂CH₂CH(CH₂OH)₂   OHC—⟨ ⟩—Br (9)
(24)

Step 5-1 | TsOH/CH₂Cl₂

(19) R—[H]—CH₂CH₂—CH(O—)₂—⟨ ⟩—Br (25) (with F, F on ring)

Step 5-2 | 1. CuCN/NMP
         2. EDA

(20) R—[H]—CH₂CH₂—CH(O—)₂—⟨ ⟩—CN (1-c) (with F, F on ring)

(where, R shows a straight chain alkyl group of carbon number 1 t 10, and the cyclohexane ring and 1,3-dioxane ring have trans configuration.)

Step 6-1. Trans-4-alkylcyclohexane carboxylic acid (16) is reduced using NaAlH₂(OC₂H₄OCH₃)₂ in toluene to obtain trans-4-alkylcyclohexylmethanol (17).

Step 6-2. Compound (17) is chlorinated using thionyl chloride under presence of pyridine to obtain trans-4-alkylcyclohexylchloromethane (18).

Step 6-3. Compound (18) is cyanated using sodium cyanide in dimethyl sulfoxide (DMSO) to obtain trans-4-alkylcyclohexylacetonitrile (19).

Step 6-4. Compound (19) is hydrolyzed using an aqueous KOH solution in ethanol and neutralized in hydrochloric acid to obtain trans-4-alkylcyclohexylacetic acid (20).

Step 6-5. Compound (20) is reduced using NaAlH₂(OC₂H₄OCH₃)₂ in toluene in the same manner as in Step 6-1 to obtain 2-(trans-4'-alkylcyclohexyl)ethane-1-ole (21).

Step 6-6. Compound (21) is brominated using PBr₃ to obtain 2-(trans-4'-alkylcyclohexyl)-1-bromoethane (22).

Step 6-7. Compound (22) and diethyl malonate are given an alkylation reaction using NaOC₂H₅ in anhydrous ethanol in the same manner as in Step 1-1 to obtain diethyl 2-(trans-4'-alkylcyclohexyl)ethylmalonate (23).

Step 6-8. Compound (23) is reduced using NaAlH$_2$(OC$_2$H$_4$OCH$_3$)$_2$ in toluene in the same manner as in Step 4-3 to obtain 2-[2'-(trans-4''-alkylcyclohexyl)ethyl]propane-1,3-diol (24).

Step 7-1. Compound (24) and compound (9) are given dehydration reaction with TsOH as a catalyst in dichloromethane in the same manner as in Step 3-2 to obtain 2-(4'-bromo-3',5'-difluorophenyl)-5-[2'-(trans-4''-alkylcyclohexyl)ethyl]-1,3-dioxane (25).

Step 7-2. Compound (25) is cyanated using CuCN in NMP in the same manner as in Step 3-2 and the nitrile copper complex formed is decomposed using EDA to obtain trans-2-(4'-cyano-3',5'-difluorophenyl)-5-[2'-(trans-4''-alkylcyclohexyl)ethyl]-1,3-dioxane (1-c) of the present invention.

BEST MODE FOR WORKING THE INVENTION

The present invention will next be explained in further detail by examples and application examples.

EXAMPLE 1

Method of making 2-pentylpropane-1,3-diol (Scheme 1).

Step 1-1. 23 g (1.0 mol) of Na was dissolved in 500 cm$^3$ of anhydrous ethanol, additions were made of 160 g (1.0 mol) of diethyl malonate and then 151 g (1.0 mol) of bromopentane, and it was refluxed for 7 hours on a hot water bath. The NaBr formed was filtered, the ethanol in the filtrate was removed, and water was #added to the residue, it was extracted with chloroform, and washed with water. The chloroform was removed, and the remaining oily substance was distilled under reduced pressure (b. p. 130° C./3 mmHg) to obtain 159 g (0.69 mol) of diethyl pentylmalonate.

Step 1-2. 34 g (0.9 mol) of LiAlH$_4$ was dispersed in 690 cm$^3$ of anhydrous THF, and 159 g (0.69 mol) of diethyl pentylmalonate was added dropwise under stirring. After the dropping was completed, it was refluxed for 2 hours in a hot water bath, and after cooling to room temperature, the excess LiAlH$_4$ was decomposed by dropwise addition of THF including 10% water. 500 cm$^3$ of concentrated hydrochloric acid was added, it was extracted with chloroform and washed in 10% HCl and water. The chloroform was removed, and the remaining oily substance was distilled under reduced pressure (b. p. 110° C./4 mmHg) to obtain 76 g (0.52 mol) of 2-pentylpropane-1,3diol).

EXAMPLE 2

Method of making 4-bromo-3,5-difluorobenzaldehyde (Scheme 2).

Step 2-1. 252 g (1.95 mol) of 2,6-difluoroaniline and 170 g (2.15 mol) of anhydrous pyridine were dissolved in 780 cm$^3$ of chloroform, and a solution of 328 g (2.05 mol) of bromine dissolved in 390 cm$^3$ of chloroform was added dropwise for 2 hours on an ice water bath while stirring, after which it was stirred for 2 hours at room temperature. After washing the reaction solution with water, the chloroform was removed, the residue was distilled under reduced pressure (b. p. 100° C./30 mmHg), and the crystals obtained were recrystallized from hexane to obtain 340 g (1.63 mol) of 4-bromo-2,6-difluoroaniline.

Step 2-2. 340 g (1.63 mol) of 4-bromo-2,6-difluoroaniline, 223 g (2.5 mol) of CuCN and 800 cm$^3$ of NMP were refluxed for 1.5 hours on a mantle heater. The reaction solution was cooled to room temperature, and after adding 300 cm$^3$ of EDA, it was poured into 2,000 cm$^3$ of water, extracted with hexane, and washed with an aqueous EDA solution and ice. The hexane was removed, and the residue was distilled under reduced pressure (b. p. 143° C./6mmHg) to obtain 108 g (0.7 mol) of 4-amino-3,5-difluorobenzonitrile.

Step 2-3. While stirring 420 cm$^3$ of concentrated H$_2$SO$_4$ on an ice water bath, 54 g (0.78 mol) of pulverized NaNO$_2$ was added at a rate that maintained a temperature under 40° C., and after the addition it was stirred in a hot water bath at 50° C. until the crystals dissolved completely. While stirring this solution on an ice water bath, 700 cm$^3$ of glacial acetic acid was added dropwise, then 108 g (0.7 mol) of 4-amino-3,5-difluorobenzonitrile was added at a rate maintaining the temperature at 20°-25° C., and after the addition was completed it was stirred at this temperature until the crystals were completely dissolved to prepare a diazonium salt solution. A solution with 143 g (1.0 mol) of CuBr dissolved in 420 cm$^3$ of 47% HBr was stirred in an ice water bath while the previously prepared diazonium salt solution was added dropwise for 2 hours, and after the dropping was completed, it was stirred on an ice water bath for 1 hour and at room temperature overnight. The crystals formed were filtered, and after washing the crystals in glacial acetic acid, they were recrystallized from a mixture of acetone and methanol to obtain 98 g (0.44 mol) of 4-bromo-3,5-difluorobenzonitrile.

Step 2-4. 167 g (0.88 mol) of SnCl$_2$ was added to 880 cm$^3$ of diethyl ether, and dried HCl gas was absorbed to saturation at room temperature. 98 g (0.44 mol) of 4-bromo-3,5-difluorobenzonitrile was added all at once to this mixture, and after stirring for i hour, it was let stand overnight. The reactant was poured into 1,000 cm$^3$ of water, and ether was distilled on a hot water bath at 50° C. The residue was extracted by adding chloroform, and after washing in water the chloroform was removed. The residue was distilled under reduced pressure (b. p. 96° C./73 mmHg) to obtain 88 g (0.40 mol) of 4-bromo-3,5-difluorobenzaldehyde.

EXAMPLE 3

Method of making trans-2-(4'-cyano-3',5'-difluorophenyl)-5-pentyl 1,3-dioxane (Scheme 3).

Step 3-1. 10.8 g (0.074 mol) of 2-pentylpropane-1,3-diol, 16.3 g of 4-bromo-3,5-difluorobenzaldehyde and 0.7 g of TsOH were dissolved in 74 cm$^3$ of dichloromethane, and was refluxed for 3 hours on a hot water bath with a Dean-Stark trap applied to remove the water formed. The reactant was washed in water, the dichloromethane was removed, and the residue was recrystallized from a mixture of acetone and methanol to obtain 9.1 g (0.026 mol) of 2-(4'-bromo-3',5'-difluorophenyl)-5-pentyl-1,3-dioxane.

Step 3-2. 9.1 g (0.026 mol) of 2-(4'-bromo-3',5'-difluorophenyl)-5-pentyl-1,3-dioxane, 3.5 g (0.0039 mol) of CuCN and 78 cm$^3$ of NMP were refluxed for 2 hours on a mantle heater. The reactant was cooled to room temperature, and after adding 10 cm$^3$ of EDA, it was poured in ice water, extracted with hexane and washed with an aqueous EDA solution and water. The hexane was removed, the residue was treated in a silica gel column with chloroform as solvent, and the chloroform was removed. The residue was recrystallized from a mixture of methanol and water to obtain 1.7 g (0.006mol) of trans-2-(4'-cyano-3',5'-difluorophenyl)-5- pentyl-1,3-dioxane. The phase transition temperature of this compound as measured using DSC was as follows.

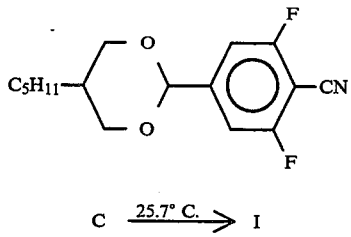

(where, C indicates crystal, and I shows isotropic liquid).

The following compounds were made by the same method of manufacture as Example 3.

Trans-2-(4'-cyano-3',5'-difluorophenyl)-5-methyl-1,3-dioxane

Trans-2 - (4'-cyano-3',5'-difluorophenyl)-5-ethyl-1,3-dioxane

Trans-2-(4'-cyano-3',5'-difluorophenyl) -5-propyl-1,3-dioxane

Trans-2-(4'-cyano-3,5'-difluorophenyl)-5-butyl 1,3-dioxane

Trans-2-(4'-cyano-3',5'-difluorophenyl)-5-hexyl-1,3-dioxane

Trans-2-(4'-cyano-3',5'-difluorophenyl)-5-heptyl-1,3-dioxane

Trans-2-(4'-cyano-3',5'-difluorophenyl)-5-octyl-1,3-dioxane

Trans-2-(4'-cyano-3',5'-difluorophenyl)-5-nonyl-1,3-dioxane

Trans-2-(4'-cyano-3,5'-difluorophenyl)-5-decyl-1,3-dioxane

EXAMPLE 4

Method of making 2-(4'-propylcyclohexyl)propane-1,3-diol (trans-cis form mixture) (Scheme 4).

Step 4-1. 142 g (1.0 mol) of 4-propylcyclohexanol (trans-cis form mixture) was given drop addition of 136 g (0.5 mol) of PBr$_3$ while stirring at room temperature, and heated to about 80° C. The reactant was stirred for 1 hour on a 70° C. hot water bath, then cooled to room temperature and poured into ice water to decompose the excess PBr$_3$. The oily layer was taken off, and the water layer was extracted with chloroform, combined with the oily layer and washed with water. The chloroform was removed, and the remaining oily substance was distilled under reduced pressure (b. p. 97° C./14 mmHg) to obtain 180 g (0.88 mol) of 4-propylbromocyclohexane (trans-cis form mixture).

Step 4-2. 31 g (1.35 mol) of sodium was dissolved in 660 cm$^3$ of anhydrous ethanol, after which 216 g (1.35 mol) of diethyl malonate and then 180 g (0.88 mol) of 4-propylbromocyclohexane were added in single additions, and it was refluxed for 10 hours on a hot water bath. The reactant was cooled to room temperature, and after filtering the NaBr crystals that had formed, the ethanol in the filtrate was removed. Water was added to the residue, it was extracted with chloroform, and washed with water. The chloroform was removed, and the remaining oily substance was distilled under reduced pressure (b. p. 138° C./1.4 mmHg) to obtain 108 g (0.38 mol) of diethyl 4-propylcyclohexylmalonate (trans-cis form mixture).

Step 4-3. 340 cm$^3$ (1.3 mol) of a 70% NaAlH$_2$(OC$_2$H$_4$OCH$_3$)$_2$ in toluene with 340 cm$^3$ of anhydrous toluene was stirred at room temperature while adding 57 g (0.2 mol) of diethyl 4-propylcyclohexylmalonate dropwise for 30 minutes, after which it was stirred for 5 hours on a hot water bath at 80°-90° C. The reactant was cooled to room temperature, and 50 cm$^3$ of water and 1,000 cm$^3$ of 15% HCl were dropped while stirring. The oily layer was removed, and the water layer was extracted with toluene and combined with the oily layer and washed with 10% HCl and water. The toluene was removed, and the residue was recrystallized from hexane to obtain 18 g (0.09 mol) of 2-(4'-propylcyclohexyl)propane-1,3-diol (trans-cis form mixture).

EXAMPLE 5

Method of making trans-2-(4'-cyano-3',5'-difluorophenyl)-5-(trans-4'-propylcyclohexyl)-1,3-dioxane (Scheme 5).

Step 5-1. 6.0 g (0.03 mol) of 2-(4'-propylcyclohexyl)propane-1,3-diol, 6.6 g (0.03 mol) of 4-bromo-3,5-difluorobenzaldehyde and 0.3 g of TsOH were dissolved in 60 cm$^3$ of dichloromethane, and it was refluxed for 3 hours on a hot water bath while removing the water produced with a Dean-Stark trap. After washing the reactant on water, the dichloromethane was removed. The residue was recrystallized from a solvent mixture of acetone and methanol to obtain 7.3 g (0.018 mol) of 2-(4'-bromo-3',5'-difluorophenyl)-5-(4'-propylcyclohexyl)-1,3-dioxane(trans-cis form mixture).

Step 5-2. 7.3 g (0.018 mol) of 2-(4'-bromo-3',5'-difluorophenyl)-5-(4'-propylcyclohexyl)-1,3-dioxane, 2.5 g (0.027 mol) of CuCN$_2$ and 54 cm$^3$ of NMP were refluxed for 2 hours with a mantle heater. After cooling the reactant to room temperature, 40 cm$^3$ of EDA was added, it was poured into 50 cm$^3$ of ice water, extracted with chloroform and washed with an aqueous EDA solution and water. The chloroform was removed, and the residue was dissolved in hexane and washed with water to remove the NMP. The hexane was removed, and the residue was treated in a silica gel column with chloroform as the solvent. The chloroform was removed, and the residue was repeatedly recrystallized in a solvent mixture of acetone and methanol until there were no cis forms to obtain 1.4 g (0.004 mol) of trans-2-(4'-cyano-3',5'-difluorophenyl)-5-(trans-4'-propylcyclohexyl)-1,3-dioxane. The phase transition temperature of this compound was measured with DSC as follows.

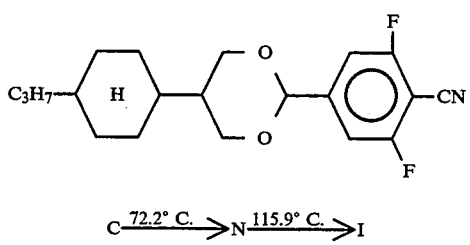

(here, C shows crystals, N shows the nematic phase and I shows isotropic liquid.)

The following compounds were made by the same method manufacture as in Example 5.

Trans-2-(4'-cyano-3',5'-difluorophenyl)-5- (trans-4'-methylcyclohexyl )-1,3-dioxane Trans-2-(4'-cyano-3',5'-difluorophenyl)-5-(trans-4'-ethylcyclohexyl )-1,3 -dioxane Trans-2-(4'-cyano-3',5'-difluorophenyl)-5-(trans-4'-butylcyclohexyl)-1,3-dioxane

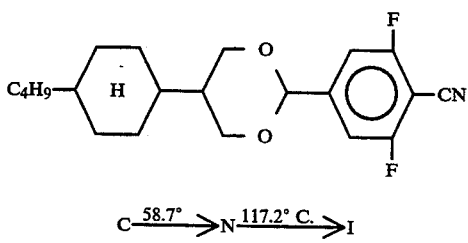

C $\xrightarrow{58.7°}$ N $\xrightarrow{117.2° \text{ C.}}$ I

Trans-2-(4'-cyano-3',5'-difluorophenyl)-5-(trans-4'-pentylcyclohexyl)-1,3-dioxane

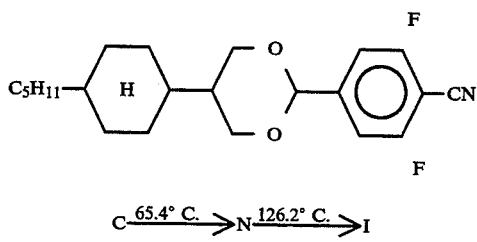

C $\xrightarrow{65.4° \text{ C.}}$ N $\xrightarrow{126.2° \text{ C.}}$ I

Trans-2-(4'-cyano-3',5'-difluorophenyl)-5-(trans-4'-hexylcyclohexyl)-1,3-dioxane

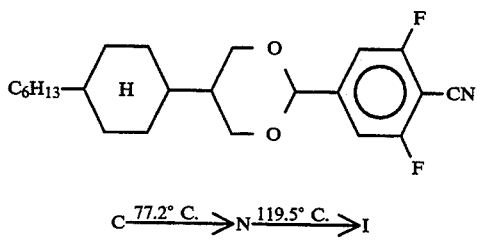

C $\xrightarrow{77.2° \text{ C.}}$ N $\xrightarrow{119.5° \text{ C.}}$ I

Trans-2-(4'-cyano-3',5'-difluorophenyl)-5-(trans-4'-heptylcyclohexyl)-1,3-dioxane
Trans-2-(4'-cyano-3',5'-difluorophenyl)-5-(trans-4'-octylcyclohexyl)-1,3-dioxane
Trans-2-(4'-cyano-3',5'-difluorophenyl)-5-(trans-4'-nonylcyclohexyl)-1,3-dioxane
Trans-2-(4'-cyano-3',5'-difluorophenyl)-5-(trans-4'-decylcyclohexyl)-1,3-dioxane

EXAMPLE 6

Method of making 2-[2'-(trans-4'- butylcyclohexyl)ethyl]propane-1,3-diol (Scheme 6).

Step 6-1. 55 g (0.30 mol) of trans-4-butylcyclohexane carboxylic acid was dispersed in 200 cm³ of toluene, and while stirring at room temperature, 250 cm³ (0.90 mol) of a 70% NaAlH₂(OC₂H₄OCH₃)₂ in toluene was added dropwise at a rate where the toluene refluxed quietly, after which it was stirred for 3 hours on a 90° C. hot water bath. The reactant was cooled to room temperature, cm³ of water and 300 cm³ of 15% HCl were added dropwise while stirring, the oily layer was taken off, the water layer was extracted with toluene and combined with the oily layer, and they were washed with 10% HCl and water. The toluene was removed, and the remaining oily substance was distilled under reduced pressure (b. p. 100° C./2 mmHg) to obtain 37 g (0.22 mol) of trans-4-butylcyclohexylmethanol.

Step 6-2. 37 g (0.22 mol) of trans-4-butylcyclohexylmethanol and 18 g (0.23 mol) of anhydrous pyridine were given dropwise addition of 32 g (0.27 mol) of SOCl₂ in an ice water bath while stirring, and then stirred for 3 hours at 105°-110° C. with a mantle heater. The reactant was cooled to room temperature, poured into a beaker containing concentrated HCl and ice, the oily layer was taken off, the water layer was extracted with chloroform, combined with the oily layer and washed with 10% HCl and water. The chloroform was extracted, and the remaining oily substance was distilled under reduced pressure (b. p. 80° C./3 mmHg) to obtain 38 g (0.20 mol) of trans-4-butylcyclohexylchloromethane.

Step 6-3. 38 g (0.20 mol) of trans-4-butylcyclohexylchloromethane, 12 g (0.24 mol) of NaCN and 40 cm³ of DMSO were heated up to 140° C. with a mantle heater while stirring. The reactant was cooled to room temperature, 1,000 cm³ of water was added, it was extracted with chloroform, and after washing with water the chloroform was extracted. The remaining oily substance was distilled under reduced pressure (b. p. 90°/3 mmHG) to obtain 34 g (0.19 mol) of trans-4-butylcyclohexylacetonitrile.

Step 6-4. 34 g (0.19 mol) of trans-4-butylcyclohexylacetonitrile, 43 g (0.76 mol) of KOH, 34 cm³ of water and 190 cm³ of ethanol were refluxed on a hot water bath until formation of ammonia gas stopped. The ethanol in the reactant was removed, the residue was dissolved in 100 cm³ of water, it was poured into a beaker containing 100 cm³ of concentrated HCl and 100 g of ice, and the deposited crystals were filtered and washed in water. The crystals were recrystallized from a solvent mixture of methanol and water to obtain 37 g (0.19 mol) of trans-4-butylcyclohexylacetic acid.

Step 6-5. 37 g (0.19 mol) of trans-4-butylcyclohexyl acetic acid was dispersed in 190 cm) of anhydrous toluene, 160 cm³ (0.57 mol) of 70% of NaAlH₂(OC₂H₄OCH₃)₂ in toluene was added dropwise while stirring at a rate where the toluene refluxed quietly, after which it was stirred for 3 hours on a 90° C. hot water bath. The reactant was cooled to room temperature, 40 cm³ of water and 500 cm³ of 15% HCl were added dropwise while stirring, the oily layer was taken off, and the water layer was extracted with toluene, combined with the oily layer and washed with 10% HCl and water. The toluene was removed, and the remaining oily substance was distilled under reduced pressure (b. p. 103° C./3 mmHg) to obtain 31 g (0.17 mol) of 2-(trans-4'-butylcyclohexyl)ethanol.

Step 6-6. 31 g (0.17 mol) of 2-(trans-4'-butylcyclohexyl)ethanol was given dropwise addition of 23 g (0.09 mol) of PBr₃ while stirring at room temperature, after which it was stirred for 1 hour on a 70° C. hot water bath. The reactant was cooled to room temperature, poured into ice water to decompose the excess PBr₃, the oily layer was taken off, and the water layer was extracted with chloroform and combined with the oily layer and washed with water. The chloroform was removed, and the remaining oily substance was distilled under reduced pressure (b. p. 99° C./2 mmHg) to obtain 32 g (0.13 mol) of 2-(trans-4'-butylcyclohexyl)-1-bromoethane.

Step 6-7. 3.0 g (0.13 mol) of sodium was dissolved in 130 cm³ of anhydrous ethanol, 26 g (0.16 mol) of diethyl malonate and 32 g (0.13 mol) of 2-(trans-4'-butylcyclohexyl)-1-bromoethane were added and it was refluxed for 5 hours on a hot water bath. The reactant was cooled to room temperature, the NaBr formed was filtered, and after removing the ethanol in the filtrate, water was added, it was extracted with chloroform and washed with water. The chloroform was removed, and the remaining oily substance was distilled under reduced pressure (b. p. 165° C./3 mmHg) to obtain g (0.10 mol) of diethyl 2-(trans-4'-butylcyclohexyl)ethylmalonate Step 6-8. 170 cm³ (0.60 mol) of 70% of NaAlH₂(OC₂H₄OCH₃)₂ in toluene was dissolved in 170 cm³ of anhydrous toluene, and after adding 36 g (0.10 mol) of diethyl 2-(trans-4'-butylcyclohexyl) ethylmalonate dropwise while stirring, it was stirred for 5 hours on a 80°–90° C. hot water bath. The reactant was cooled to room temperature, 30 cm³ of water and 500 cm³ of 15% HCl were added dropwise while stirring, and the oily layer was taken off, the water layer was extracted with toluene, combined with the oily layer and washed in 10% HCl and water. The toluene was removed, and the residue was recrystallized from hexane to obtain 18 g (0.08 mol) of 2-[2'-(trans-4''-butylcyclohexyl)ethyl]propane-1,3-diol.

EXAMPLE 7

Method of making trans-2-(4'-cyano-3',5'-difluorophenyl)-5-[2'-(trans-4'-butylcyclohexyl)ethyl]-1,3-dioxane (Scheme 7).

Step 7-1. 7.3 g (0.03 mol) of 2-[2'-(trans-4'-propylcyclohexyl)ethyl]propane-1,3-diol, 6.6 g (0.03 mol) of 4-bromo-3,5-difluorobenzaldehyde, 0.3 g of TsOH and 60 cm³ of dichloromethane were refluxed for 3 hours in a hot water bath while removing the water formed with a Dean-Stark trap. The reactant was washed with water, the dichloromethane was removed, and the residue was recrystallized from a solvent mixture of acetone and methanol to obtain 7.6 g (0.017 mol) of 2-(4'-bromo-3',5'-difluorophenyl)-5-[2'-trans-4''-butylcyclohexyl)ethyl]-1,3-dioxane.

Step 7-2. 7.6 g (0.017 mol) of 2-(4'-bromo-3',5'-difluorophenyl)-5-[2'-(trans-4''-butylcyclohexyl)ethyl]-1,3-dioxane, 2.3 g (0.026 mol) of CuCN and 52 cm³ of NMP were refluxed for 2 hours with a mantle heater. The reactant was cooled to room temperature, and after adding 4 cm³ of EDA it was poured into 100 cm³ of ice water, extracted with hexane and washed with an aqueous EDA solution and water. The hexane was removed, and it was treated in a silica gel column with chloroform as the solvent. The chloroform was removed, and the residue was recrystallized from a solvent mixture of acetone and methanol to obtain 2.2 g (0.006 mol) of trans-2-(4'-cyano-3',5'-dibluorophenyl)-5-[2'-(trans-4''-butylcyclohexyl)ethyl]-1,3-dioxane. The phase transition temperature of this compound was measured with DSC as follows.

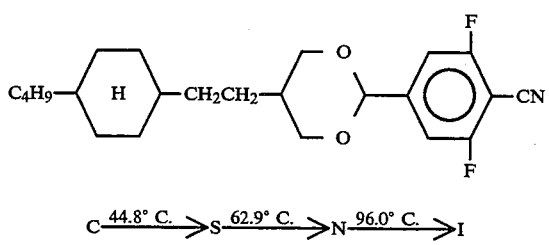

C $\xrightarrow{44.8° C.}$ S $\xrightarrow{62.9° C.}$ N $\xrightarrow{96.0° C.}$ I (where, C shows crystals, S shows the smectic phase, N shows the nematic phase and I shows isotropic liquid.)

The following compounds were made by the same method of manufacture as in Example 7.

Trans-2-(4'-cyano-3',5'-difluorophenyl)-5-[2'-(trans-4'-methylcyclohexyl)ethyl]-1,3-dioxane Trans-2-(4'-cyano-3',5'-difluorophenyl)-5-[2,-(trans-4'-ethylcyclohexyl)ethyl]-1,3-dioxane Trans-2-(4'-cyano-3',5'-difluorophenyl)-5-[2'-(trans-4'-propylcyclohexyl)ethyl]-1,3-dioxane

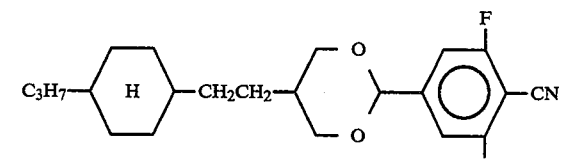

C $\xrightarrow{76.8° C.}$ N $\xrightarrow{98.2° C.}$ I

Trans-2-(4'-cyano-3',5'-difluorophenyl)-5-[2,-(trans-4'-Pentylcyclohexyl)ethyl]-1,3-dioxane

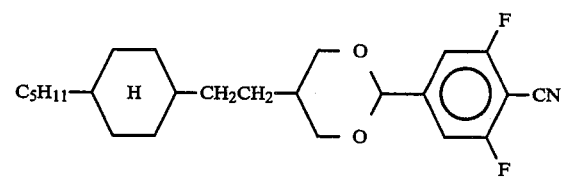

C $\xrightarrow{73.0° C.}$ N $\xrightarrow{104.0° C.}$ I

Trans-2-(4'-cyano-3',5'-difluorophenyl)-5-[2'-(trans-4'-hexylcyclohexyl)ethyl]-1,3-dioxane

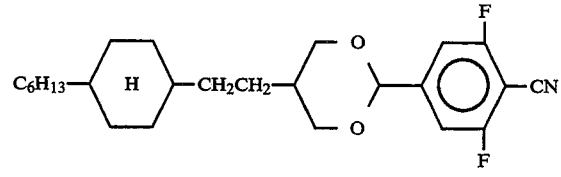

C $\xrightarrow{62.0° C.}$ N $\xrightarrow{96.8° C.}$ I

Trans-2-(4'-cyano-3',5'-difluorophenyl)-5-[2'-(trans-4'-heptylcyclohexyl)ethyl]-1,3-dioxane Trans-2-(4'-cyano-3',5'-difluorophenyl)-5-[2'-(trans-4'''-octylcyclohexyl)ethyl]-1,3-dioxane Trans-2-(4'-cyano-3',5'-difluorophenyl)-5-[2'-(trans-4'''-nonylcyclohexyl)ethyl]-1,3-dioxane Trans-2-(4'-cyano-3',5'-difluorophenyl)-5-[2'-(trans-4'-decyclohexyl)ethyl]-1,3-dioxane

APPLICATION EXAMPLE 1

The compound of the present invention and compounds (A) and (B) as comparative examples were each mixed separately at 10 wt % with 90 wt % of commercial liquid crystal composition ZLI-1565 (made by Merck Company) to prepare liquid crystal compositions.

| | |
|---|---|
| Liquid crystal composition [1] ZLI-1565 | 90 wt % |

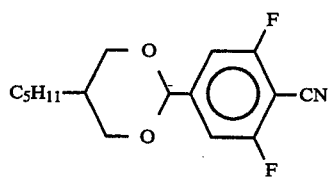

10 wt %

Liquid crystal composition [2]  
ZLI-1565                                90 wt %

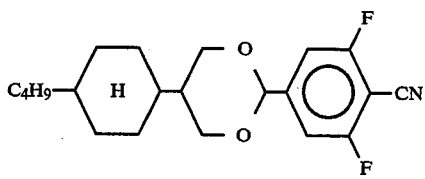

10 wt %

Liquid crystal composition [3]  
ZLI-1565

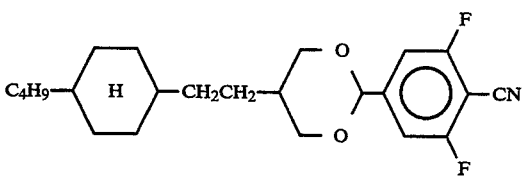

10 wt %

Liquid crystal composition [Comparative Example 1]  
ZLI-1565                                90 wt %

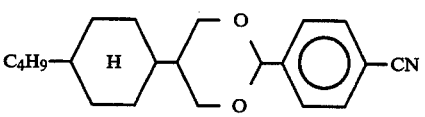

10 wt %

Liquid crystal composition [Comparative Example 2]  
ZLI-1565                                90 wt %

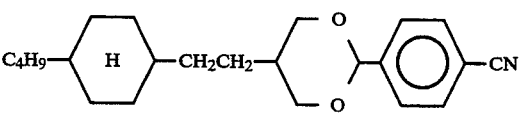

10 wt %

The N-I points and Δn of these liquid crystal compositions were measured. Next, these liquid crystal compositions were enveloped in TN type cells with cell thicknesses of 9 μm, and measurements were made of the threshold voltage ($V_{th}$) of the voltage-light transmissivity properties, steepness ($\beta$), visual angle dependence ($\alpha$) at 20° C. and the $V_{th}$ temperature dependence ($\Delta T$) and voltage margin (M) at V−3V and ⅓ duty at 40° C. Here, $\alpha$, $\beta$, $\Delta T$ and M were measured by the following formulas.

$$\alpha = \frac{V_{10}(T = 20°, \phi = 10°)}{V_{10}(T = 20° C., \phi = 40°)}$$

$$\beta = \frac{V_{90}(T = 20°, \phi = 10°)}{V_{90}(T = 20° C., \phi = 40°)}$$

$$\Delta T = V_{10}(T = 0° C., \phi = 10°) - V_{10}(T = 40°, \phi = 10°) \quad (V)$$

$$M = \frac{V_{10}(T = 40° C., \phi = 40°) - V_{90}(T = 0°, \phi = 10°)}{V_{10}(T = 40° C., \phi = 40°) + V_{90}(T = 0°, \phi = 10°)} \times 100(\%)$$

(where, $V_{10}$ and $V_{90}$ are respectively the threshold voltage and saturation voltage, light transmissivity is 10% and 90%, and represents temperature and $\phi$ the visual angle.)

The above results are shown in Table 1.

TABLE 1

| Composition | N-I$_{point}$ (°C.) | Δn | $V_{th}$(V) | α | β | ΔT(V) | M(%) |
|---|---|---|---|---|---|---|---|
| [1] | 73.9 | 0.122 | 1.81 | 1.29 | 1.40 | −0.37 | 8.1 |
| [2] | 88.7 | 0.127 | 2.03 | 1.30 | 1.40 | −0.27 | 10.0 |
| [3] | 86.5 | 0.125 | 2.00 | 1.29 | 1.39 | −0.30 | 9.5 |
| Comparative Example 1 | 96.4 | 0.128 | 2.48 | 1.32 | 1.47 | −0.30 | 8.5 |
| Comparative Example 2 | 92.5 | 0.128 | 2.45 | 1.31 | 1.48 | −0.31 | 8.2 |

APPLICATION EXAMPLE 2

Liquid crystal compositions [4], [5], [6], [7] and [8] were made from the following components.

Liquid crystal compositions [4]
[Numbers:] wt %
LC composition [4]
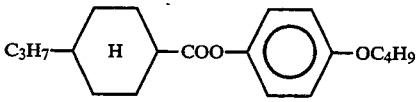 8.9 wt %
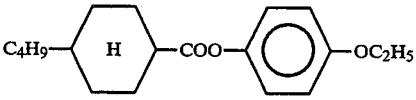 7.0 wt %
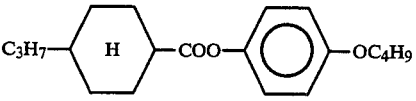 7.5 wt %
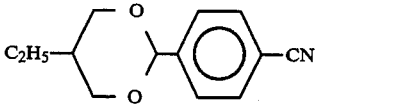 10.4 wt %
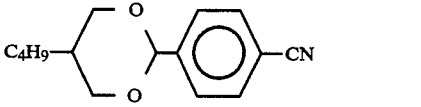 15.6 wt %
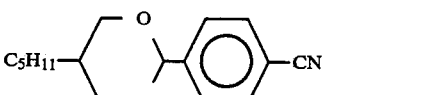 15.6 wt %
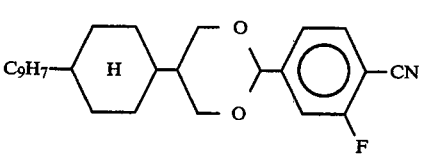 5.0 wt %
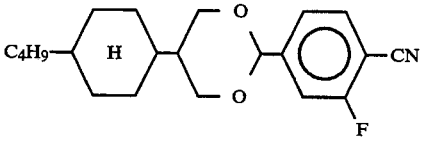 5.0 wt %
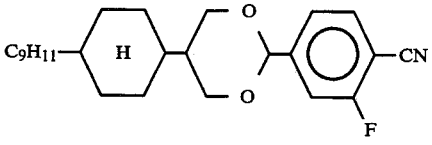 5.0 wt %
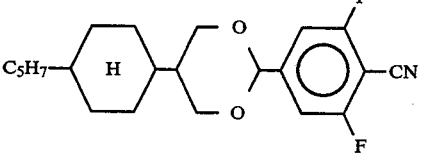 5.0 wt %
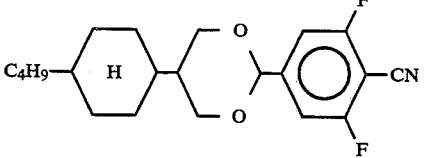 5.0 wt %

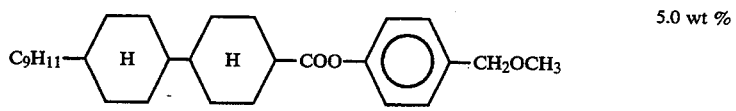 5.0 wt %
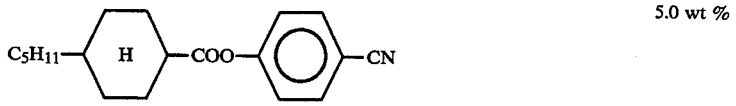 5.0 wt %
Liquid crystal composition [5]
[Numbers:] wt %
(trans form about 80%)
LC composition [5]
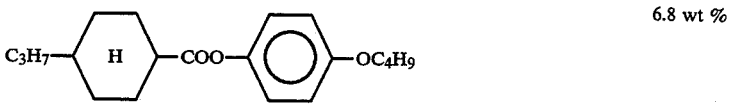 6.8 wt %
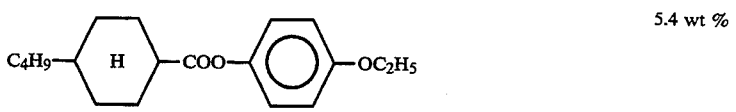 5.4 wt %
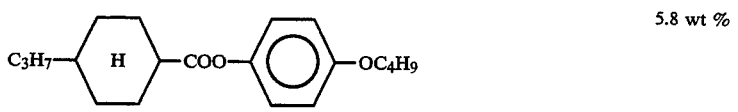 5.8 wt %
 8.0 wt %
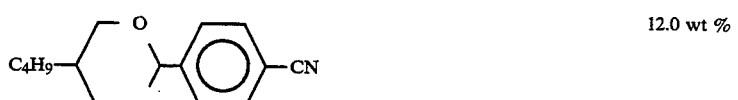 12.0 wt %
 12.0 wt %
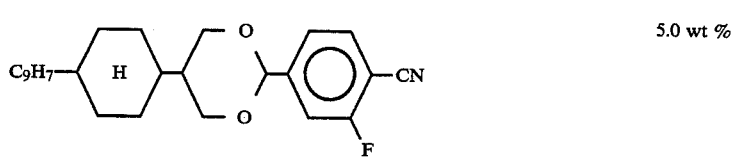 5.0 wt %
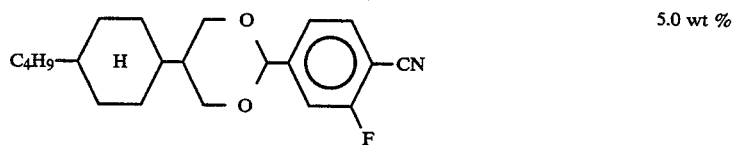 5.0 wt %
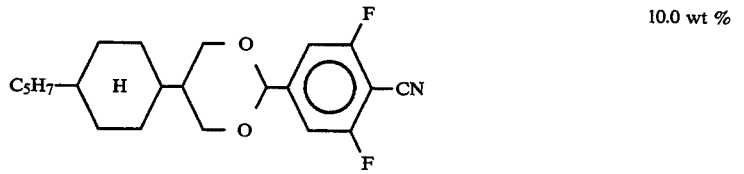 10.0 wt %

-continued
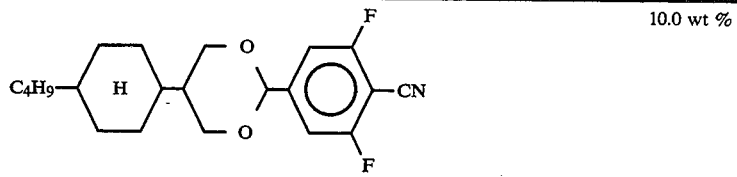 10.0 wt %
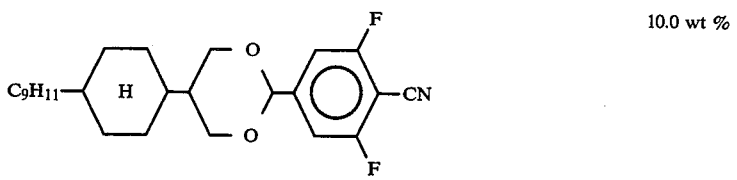 10.0 wt %
 5.0 wt %
Trans form about 80%)
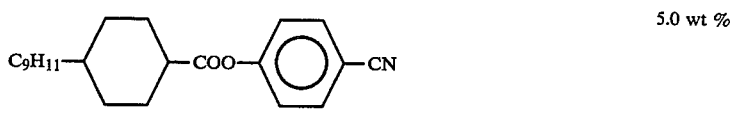 5.0 wt %
Liquid crystal composition [6]
[Numbers:] wt %
LC composition [6]
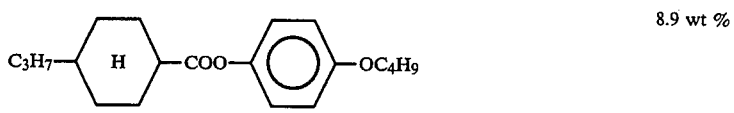 8.9 wt %
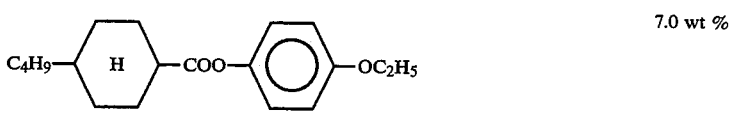 7.0 wt %
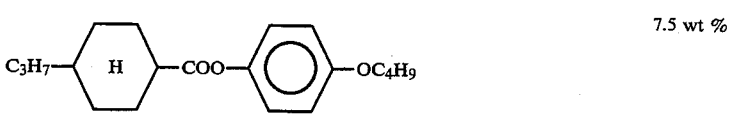 7.5 wt %
 10.4 wt %
 15.6 wt %
 15.6 wt %
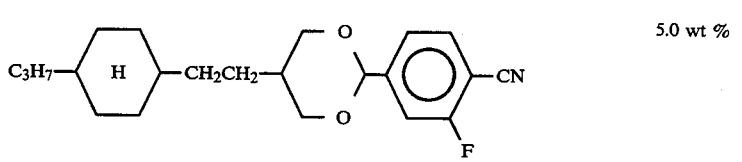 5.0 wt %

-continued
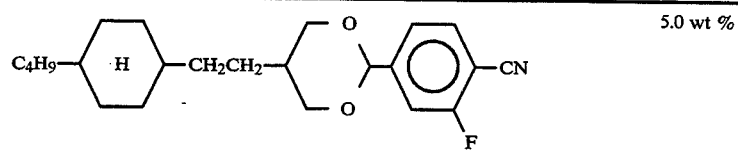
5.0 wt %
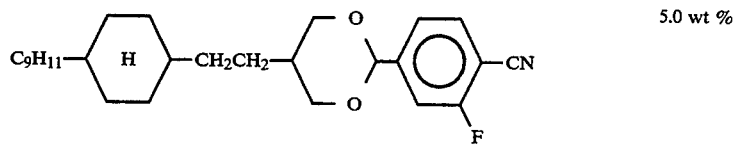
5.0 wt %
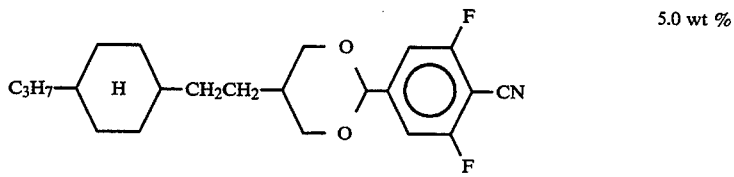
5.0 wt %
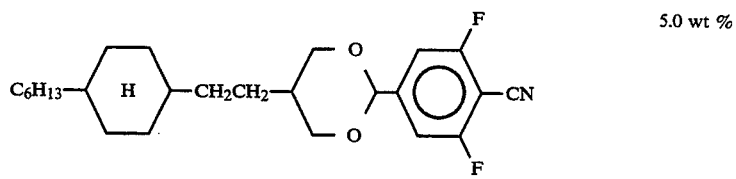
5.0 wt %
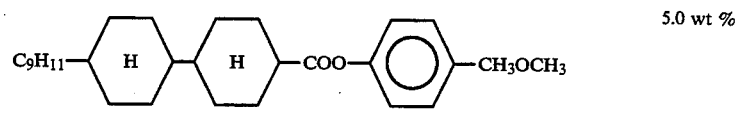
5.0 wt %
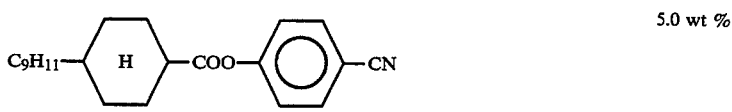
5.0 wt %
Liquid crystal composition [7]
[Numbers:] wt %
(trans form about 80%)
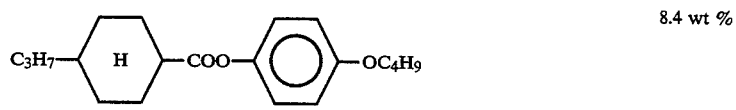
8.4 wt %
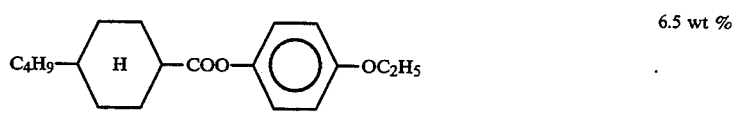
6.5 wt %
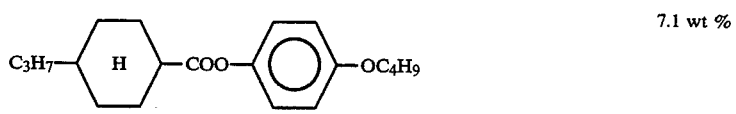
7.1 wt %
9.8 wt %
14.6 wt %

-continued
 14.6 wt %
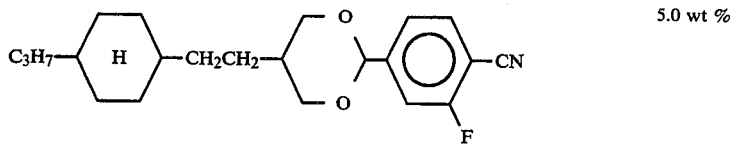 5.0 wt %
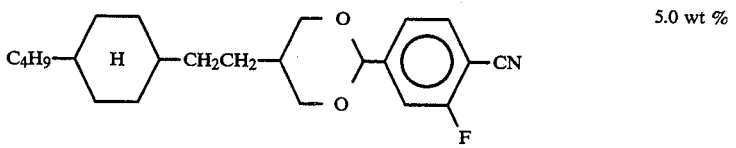 5.0 wt %
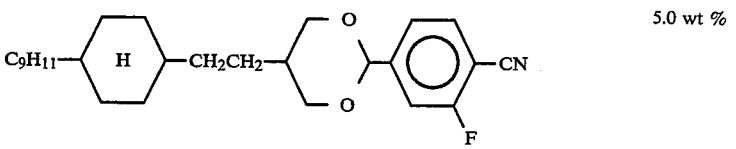 5.0 wt %
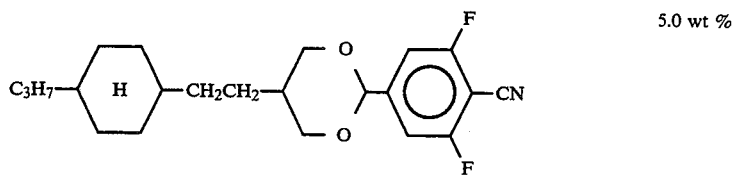 5.0 wt %
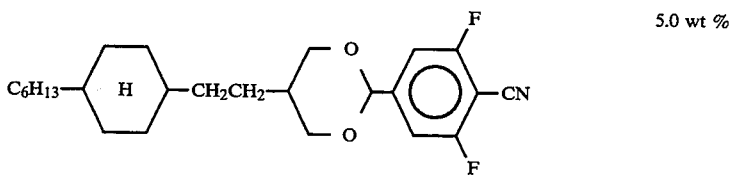 5.0 wt %
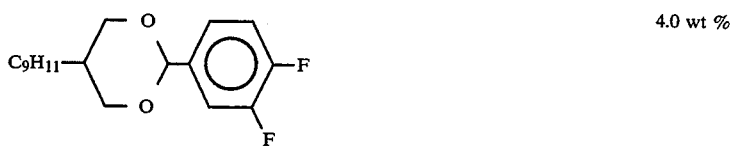 4.0 wt %
trans form about 80%)
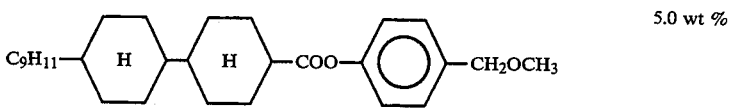 5.0 wt %
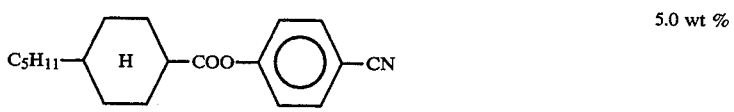 5.0 wt %
Liquid crystal composition [8]
[Numbers:] wt %
(trans form about 80%)
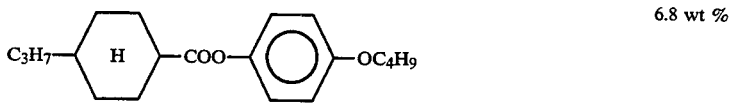 6.8 wt %

| | |
|---|---|
| 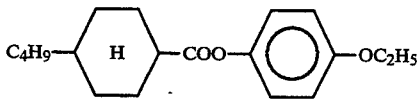 | 5.4 wt % |
| 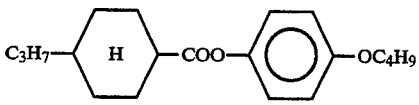 | 5.8 wt % |
| 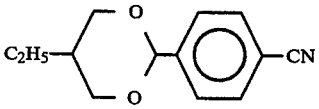 | 8.0 wt % |
| 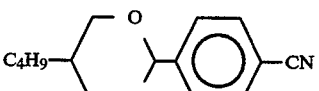 | 12.0 wt % |
| 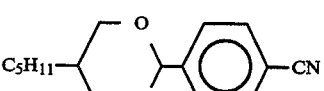 | 12.0 wt % |
| 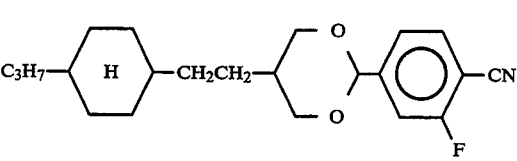 | 5.0 wt % |
| 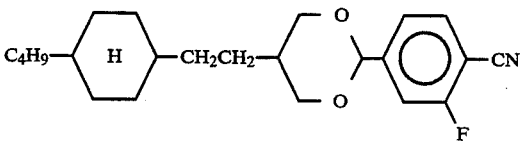 | 5.0 wt % |
| 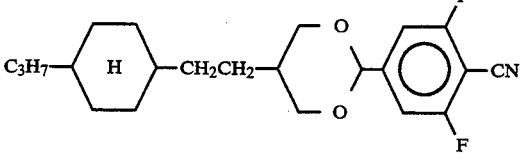 | 10.0 wt % |
| 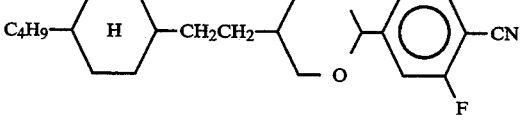 | 10.0 wt % |
| 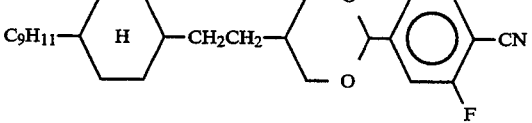 | 10.0 wt % |
| 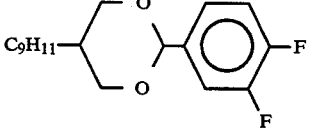 | 5.0 wt % |
about form about 80%)

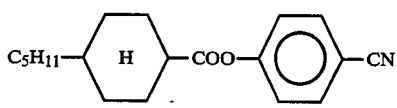

5.0 wt %

The N-I point, Δn, $V_{th}$, α, β, ΔT and M of these liquid crystal compositions were measured in the same manner as in Application Example 1, and the results are shown in Table 2.

TABLE 2

| Composition | N-I$_{point}$ (°C.) | Δn | $V_{th}$(V) | α | β | ΔT(V) | M(%) |
| --- | --- | --- | --- | --- | --- | --- | --- |
| [4] | 75.1 | 0.108 | 1.15 | 1.28 | 1.47 | 0.343 | 6.3 |
| [5] | 67.8 | 0.102 | 0.91 | 1.28 | 1.48 | 0.423 | 4.5 |
| [6] | 70.4 | 0.105 | 1.14 | 1.28 | 1.45 | 0.391 | 5.5 |
| [7] | 65.5 | 0.100 | 1.07 | 1.26 | 1.48 | 0.440 | 4.0 |
| [8] | 61.7 | 0.099 | 0.87 | 1.29 | 1.49 | 0.376 | 5.3 |

From the results above, it will be understood that the liquid crystal composition of the present invention is capable of high time sharing drive even under low $V_{th}$ voltage below 1 V.

POSSIBILITY OF INDUSTRIAL UTILIZATION

As described above, the 1,3-dioxane derivative of the present invention has a very large Δε, and a small Δn.

Also, it can be confirmed that liquid crystal compositions obtained by mixing the 1,3-dioxane derivative of the present invention with prior liquid crystal compounds have wide visual angles and are capable of high time sharing drive at low voltages.

Consequently, the 1,3-dioxane derivative of the present invention is very useful as a liquid crystal compound or analog compound used in liquid crystal display apparatus of the TN type or STN type.

What is claimed is:

1. A 1,3-dioxane derivative having the general formula

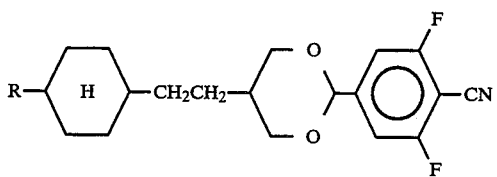

wherein R is a straight chain alkyl group of carbon number 1 to 10, and the cyclohexane ring and 1,3-dioxane ring are respectively in trans form.

2. A liquid crystal composition comprising at least one 1,3-dioxane derivative having the general formula:

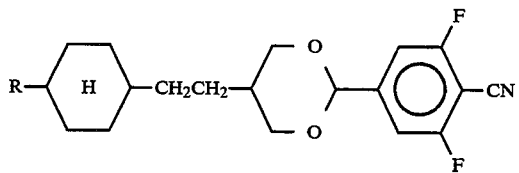

wherein R is a straight chain alkyl group of carbon number 1 to 10, and the cyclohexane ring and 1,3-dioxane ring are respectively in trans form.

3. The liquid crystal composition of claim 2, wherein the 1,3-dioxane derivative is present as 1 to 30 wt % of the composition.

* * * * *